United States Patent [19]
Ragunathan et al.

[11] Patent Number: 6,028,065
[45] Date of Patent: Feb. 22, 2000

[54] FLOCCULATED SUSPENSION OF MEGESTROL ACETATE

[75] Inventors: Narayan Ragunathan, Nanuet, N.Y.; James C. Chao, Warren; Robert A. Femia, Kinnelon, both of N.J.; Malcolm S. F. Ross, Tel Aviv, Israel

[73] Assignee: Pharmaceutical Resources, Inc., Spring Valley, N.Y.

[21] Appl. No.: 09/063,241

[22] Filed: Apr. 20, 1998

[51] Int. Cl.⁷ .............................. A61K 9/10; A61K 31/56
[52] U.S. Cl. ............................. 514/178; 424/722
[58] Field of Search .............................. 424/722; 514/178

[56] References Cited

U.S. PATENT DOCUMENTS

| | | | |
|---|---|---|---|
| 3,356,573 | 12/1967 | Kirk et al. | 167/74 |
| 4,370,321 | 1/1983 | Greaney et al. | 424/243 |
| 4,396,615 | 8/1983 | Petrow et al. | 424/242 |
| 4,666,885 | 5/1987 | Labrie | 514/15 |
| 4,760,053 | 7/1988 | Labrie | 514/15 |
| 4,775,661 | 10/1988 | Labrie | 514/15 |
| 5,338,732 | 8/1994 | Atzinger et al. | 514/178 |

Primary Examiner—Peter F. Kulkosky
Attorney, Agent, or Firm—Ostrolenk, Faber, Gerb & Soffen, LLP

[57] ABSTRACT

A novel oral pharmaceutical composition in the form of a stable flocculated suspension in water is described as comprising: megestrol acetate; at least one compound selected from the group consisting of polyethylene glycol, propylene glycol, glycerol, and sorbitol; and a surfactant, wherein polysorbate and polyethylene glycol are not simultaneously present.

19 Claims, No Drawings

FLOCCULATED SUSPENSION OF MEGESTROL ACETATE

FIELD OF THE INVENTION

The present invention relates to a composition containing megestrol acetate which is the generic name for 17-α-acyloxy-6-methylpregna-4,6 diene-3,20-dione.

BACKGROUND OF THE INVENTION

Megestrol acetate is a steroid compound known for its anti-neoplastic activity.

Kirk et al., U.S. Pat. No. 3,356,573, disclose a megestrol acetate pharmaceutical tablet preparation comprising lactose, magnesium stearate and starch. Kirk, et al, also disclose that liquid compositions of megestrol acetate can be useful but provided no details as to the composition of such formulations.

Petrow et al., U.S. Pat. No. 4,396,615, disclose a method of treating androgen-related disorders by administering 6-methyleneprogesterone derivatives concurrently with megestrol acetate. However, Petrow et al. but do not elaborate on what constitutes the megestrol acetate formulation.

Greaney et al., U.S. Pat. No. 4,370,321, disclose adjuvant therapy for the treatment of breast cancer employing megestrol acetate. However, the type or composition of the megestrol acetate formulation is not specifically described.

Labrie, U.S. Pat. No. 4,666,885, discloses combination therapy for treatment of female breast cancer comprising the administration of luteinizing hormones in combination with an anti-androgen compound such as megestrol acetate. In particular, Labrie discloses that the anti-androgens are formulated with conventional pharmaceutical excipients (e.g., spray dried lactose and magnesium stearate) into tablets or capsules for oral administration.

Labrie, U.S. Pat. No. 4,760,053 discloses methods of treating sex steroid dependent cancers by combination therapy which includes the use of megestrol acetate. However, Labrie does not describe the type or composition of pharmaceutical formulation used in the treatment.

Labrie, U.S. Pat. No. 4,775,661, discloses methods of treating female breast cancer with a combination therapy in which megestrol acetate is disclosed as a suitable steroidal anti-androgen. Labrie also discloses that megestrol acetate, as an active substance, may be mixed with binders such as polyethylene glycol and may include taste improving substances which can be worked into tablets or dragee cores.

Since the use of megestrol acetate is widespread in clinical medicine, it would be desirable to have a liquid pharmaceutical dosage in a flocculated form for use in those cases where patients are unable to swallow tablets or capsules or where a high dose would require the ingestion of a relatively large number of tablets. Unfortunately, the formulation of a flocculated suspension which is stable is difficult in the case of megestrol acetate.

Atzinger et al., U.S. Pat. No. 5,338,732, point out the distinction between a flocculated suspension and suspensions in general and point out that the stability of a flocculated suspension of a steroid such as megestrol acetate can be critically dependent on concentration. Furthermore, they also disclose that megestrol acetate flocculated suspensions are unique because what would otherwise be predictable based on the prior art teachings does not apply when the drug is megestrol acetate. For instance, it is well known in the art prior to Atzinger et al. that megestrol acetate, a hydrophobic solid, is not easily wetted by water and has a relatively high interfacial tension accentuated by entrapped air absorbed on the surface of the particle. Hence, the use of surfactants are required to provide a suspension and maintain physical stability. According to Atzinger et al., the amount and type of surfactants are particularly critical in providing a stable floc. The flocculated suspension of megestrol acetate of Atzinger et al. uses megestrol acetate micronized so that 90% of the weight of particles is below 20 microns and the mass median diameter is between 3.0 and 10 microns, and requires that the micronized particles are dispersed in water with polysorbate 80 and polyethylene glycol to reduce interfacial tension between the particle, entrapped gas and water.

According to R. A. Nash, Chap. 5, page 181, (Pharmaceutical Suspensions, Pharmaceutical Dosage Forms, Marcel Decker, New York) the usual concentration of a surfactant varies from 0.05 to 0.5% w/v and depends on the solids content intended for suspension. Examples of such suspensions are given in Table 1 which lists some currently marketed steroid suspensions (1989 Physicians Desk Reference, 43rd Edition) and the polysorbate 80 surfactant concentration.

TABLE 1

Percent of Polysorbate 80 Concentration Used in Steroid Suspensions According to R.A. Nash, Chap. 5, page 181, (Pharmaceutical Suspensions, Pharmaceutical Dosage Forms, Marcel Decker, New York)

| Steroid | Steroid Conc. mg/ml | Polysorbate 80 percent w/v |
| --- | --- | --- |
| Aristocort Forte | 40 | 0.2 |
| Artistospan | 20 | 0.4 |
|  | 5 | 0.2 |
| Cortone Acetate | 25 to 50 | 0.4 |
| Decadron - LA | 8 | 0.075 |
| Depo-Provera | 100 | 0.184 |
| Hydeltra-T.B.A. | 20 | 0.1 |
| Hydrocortone Acetate | 25 to 50 | 0.4 |
| Kenalog-40 | 40 | 0.04 |

As taught by Atzinger et al., megestrol acetate suspensions prepared using polysorbate concentrations as indicated above are not stable in that deflocculation and caking occurs. Therefore, they state that in order to achieve a stable flocculated megestrol acetate suspension, polysorbate must be used at a concentration at about or less than 0.02% w/v, preferably from 0.005% to 0.015% w/v and most preferably 0.01% w/v, in combination with polyethylene glycol. At polysorbate 80 concentrations as low as 0.025% w/v, there is significant deflocculation and caking. They also state that at polysorbate concentrations at or below 0.005–0.01% w/v, a physically stable product was obtained but there is increased difficulty with respect to wetting of the micronized megestrol acetate at these low concentrations. Atzinger at al. further state that only surfactants having properties similar to polysorbate 80 can also be used. In this regard, they list polysorbate 20, 40, 60, 65 and 85 as having acceptable wetting properties.

Surprisingly, the present invention provides for different formulations of flocculated megestrol acetate suspensions which are also stable.

SUMMARY OF THE INVENTION

It is, therefore, an object of the invention to provide a liquid composition of megestrol acetate in the form of a flocculated suspension.

In one embodiment, the present invention provides an oral pharmaceutical composition in the form of a stable flocculated suspension in water comprising:

a) megestrol acetate;
b) at least one compound selected from the group consisting of polyethylene glycol, propylene glycol, glycerol, and sorbitol; and
c) a surfactant,
    wherein polysorbate and polyethylene glycol are not simultaneously present in said composition.

In another embodiment of the invention, the present invention provides an oral pharmaceutical composition in the form of a stable flocculated suspension in water comprising on a percent weight/volume basis about 2–6%, preferably about 4% megestrol acetate, about 0.0001–0.03% surfactant, up to about 40% of at least one compound selected from the group consisting of polyethylene glycol, propylene glycol, glycerol, and sorbitol, about 0.5–15% carrier and flavor, and the remainder water.

Other objects and advantages of the present invention will become apparent from the following description and appended claims.

DETAILED DESCRIPTION OF THE INVENTION

In accordance with the invention, a flocculated suspension of megestrol acetate can surprisingly be formulated in the presence of any surfactant and at least one compound selected from the group consisting of polyethylene glycol, propylene glycol, glycerol, and sorbitol.

A suspension is made up of a particular matter suspended uniformly in a medium but not soluble in it. Individual solute molecules do not bond tightly to form a cake in a flocculated suspension due to the fact that they form an open network aggregate with many branch points in the primary structure which prevents individual floccules from approaching each other closely. Flocculated suspensions have a high sedimentation height, due to the natural tendency for an open network aggregate to not form a cake. The resulting sediment is loosely packed and possesses a scaffold-like structure. Particles do not bond tightly to each other and a hard, dense cake does not form. Therefore, the sediment is easy to redisperse, so as to reform the original suspension. These properties make the flocculated suspension very desirable, particularly for liquid pharmaceutical formulations.

On the other hand, in a deflocculated suspension, cakes form due to the lack of wetting of the solute, which is particularly true for hydrophobic solutes such as megestrol. For instance, in the absence of appropriate wetting agents, individual megestrol particles clump and cake so as to minimize energetically unfavorable interactions between a hydrophobic solute (megestrol) and the bulk water. The hydrophobic solute packs down more over time due to the eventual release of water molecules from the inner portion of the cake which were physically trapped when cake formation began. Eventually, water molecules work their way out and surrounding solute molecules collapse into the void they leave behind. When a hard cake is formed, it is difficult, if not impossible, to redisperse.

The surfactants in a stable flocculated suspension need to be selected carefully and be used within a critical concentration range because even minor changes can have an effect on the properties of such a stable formulation. This is particularly true for megestrol acetate because predictability based on prior art teachings does not apply in this case, as noted hereinabove. What is surprising about the present invention is that any surfactant can effectively wet megestrol acetate and together form a stable flocculated suspension in the presence of at least one compound selected from the group consisting of polyethylene glycol, propylene glycol, glycerol, and sorbitol.

The surfactant can be anionic, cationic or non-ionic.

Suitable cationic surfactants include for example cetyldimethylethylammonium bromide and quaternary amines.

Suitable anionic surfactants include for example salts of sulphonic or monoesterified sulphuric acids such as alkyl benzene sulphonate, alkyl sulphates, alkyl ether sulphates, olefin sulphonates, alkyl phenol sulphates, alkyl phenol ether sulphates, alkyl ethanolamine sulphate, alkyl ethanolamine ether sulphates, alpha sulpho fatty acids or esters. Other suitable anionic surfactants include fatty alkyl sulphosuccinates, fatty alkyl ether sulphosuccinates, acyl sarcosinates, acyl taurides, and paraffin sulphonates. The preferred anionic surfactants are salts of alkali metals or alkaline earth metals, preferably sodium such as docusate sodium, sodium lauryl sulfate. Other salts include ammonium, monoethanolamine, diethanolamine, triethanolamine and alkyl amines having up to 7 aliphatic carbon atoms.

Suitable non-ionic surfactants include for example alkanolamides, ethoxylated alcohols, carboxylic acids, amines, alcohol amides, alcohol phenol, glyceryl esters, sorbitan esters, polyoxyethylene esters, phosphate esters etc. The preferred non-ionic surfactants are polysorbate, nonoxynol and polyoxyethylene glycol fatty acid esters. Amphoteric surfactants may also be used.

Wetting of a non-polar solute such as megestrol acetate takes place because it forms an association complex through Van der Waals interactions with a hydrophobic moiety of the surfactant. This effectively wets the material because the hydrophobic group of the surfactant is sequestering the megestrol while the hydrophilic group of the surfactant is solubilized in the bulk water. What is particularly surprising about the present invention is that any surfactant regardless of the length of the hydrophobic contact area on its hydrophobic group can effectively wet megestrol acetate and together form a stable flocculated suspension if at least one compound selected from the group consisting of polyethylene glycol, propylene glycol, glycerol, and sorbitol is present.

In one embodiment of the present invention, the surfactant of the present invention has a straight carbon chain of up to 20, preferably 4–20 atoms in the hydrophobic group. In a preferred embodiment, the straight carbon chain of the surfactant is less than 10 atoms. The most surprising aspect of the present invention is the fact that surfactants with such a relatively short straight chain hydrophobic group, less than 10 carbon atoms in length, wet megestrol and form a stable flocculated suspension. Such agents would normally not be expected to effectively wet megestrol acetate. A relatively short straight chain hydrophobic group such as the one on docusate (two hexyl chains, i.e. two 6 carbon length of straight chain in the hydrophobic group) presents a very small hydrophobic contact area with which the megestrol acetate molecule can associate.

In another embodiment of the present invention, the concentration of megestrol acetate in the flocculated suspension is preferably about 10 to 200 mg per ml, more preferably about 20 to 60 mg per ml and most preferably about 40 mg per ml. It is preferred that the megestrol acetate is micronized so that 90% of the weight of particles is below 20 microns and the mass median diameter is between 3.0 and 10 microns.

In yet another embodiment of the present invention, the surfactant is docusate sodium, preferably at a concentration of about 0.0001 to 0.03% weight/volume, and more preferably about 0.005 to 0.02% weight/volume.

The presence of at least one compound selected from the group consisting of polyethylene glycol, propylene glycol, glycerol, and sorbitol is critical to the suspendability of megestrol acetate in a flocculated composition. This compound is preferably up to 40%, more preferably 5–30%, and most preferably 10–25% weight/volume of the composition. In yet another embodiment, a mixture of glycerol and sorbitol is used, preferably each at a concentration of up to about 20%, and more preferably, about 5–15% weight/volume of glycerol and about 5–15% weight/volume of sorbitol.

Conventional pharmaceutical carriers can be present. Xanthan gum is preferably used as a suspending agent at about 0.1–0.35% weight/volume, and more preferably about 0.15–0.25% w/v. The use of a suspending agent maintains the megestrol acetate particles in a uniformly suspended state for a longer period of time during the dose administration period thereby permitting uniform dosing. Xanthan gum is a high molecular weight polysaccharide having thixotropic properties with immediate viscosity recovery.

Conventional preservatives, buffers, sweeteners and flavoring agents are employed. In this regard, citric acid and sodium citrate are preferred as buffers, more preferably at concentrations of about 0.3% and 0.06% weight/volume, respectively. Sodium benzoate is preferred as a preservative particularly at a concentration of about 0.1–0.3% weight/volume. Sucrose is preferred as a sweetener particularly at a concentration of about 5% weight/volume. Lemon flavor is preferred as a flavoring agents particularly at a concentration of about 0.08% weight/volume.

In a preferred embodiment, the present invention provides an oral pharmaceutical composition in the form of a stable flocculated suspension in water comprising on a percent weight/volume basis about 4% megestrol acetate, about 0.0001–0.030% docusate sodium, up to about 20% glycerol, up to about 20% sorbitol, about 0.1–0.35% xanthan gum, about 0.1–0.3% sodium benzoate, about 0.3% citric acid, about 0.06% sodium citrate, about 5% sucrose, about 0.08% flavor, and the remainder water.

EXAMPLE 1

A lemon-flavored oral suspension containing 40 mg of megestrol acetate per milliliter was prepared with a list of ingredients according to Table 2.

TABLE 2

Formulation for Megestrol Acetate Suspension

| Ingredients | % weight/volume |
| --- | --- |
| 1. Megestrol Acetate USP | 4.000 |
| 2. Glycerol USP | 5.000 |
| 3. Sorbitol NF | 15.000 |
| 4. Docusate Sodium USP | 0.002 |
| 5. Xanthan Gum NF | 0.250 |
| 6. Sodium Benzoate NF | 0.200 |
| 7. Citric Acid USP | 0.300 |
| 8. Sodium Citrate USP | 0.060 |
| 9. Sucrose NF | 5.000 |
| 10. Lemon Flavor | 0.080 |
| 11. Purified Water USP | 70.108 |

Preparation of the megestrol acetate suspension using the above-proportional amounts of ingredients is carried out as follows. Glycerol, sorbitol and docusate sodium are combined in water to form a solution. Next, xanthan gum is added to this solution in order to uniformly hydrate the gum. The citrates, sucrose, sodium benzoate, and flavor are then added to the gum dispersion and the gum slurry passed through a screen. Next, megestrol acetate is added to the gum dispersion to provide a uniform suspension. The entire suspension is then passed through a colloid mill or homogenizer to provide an oral suspension containing 40 mg/ml of megestrol acetate.

EXAMPLE 2

A lemon-flavored oral suspension containing 40 mg of megestrol acetate per milliliter was prepared with a list of ingredients according to Table 3.

TABLE 3

Formulation for Megestrol Acetate Suspension

| Ingredients | % weight/volume |
| --- | --- |
| 1. Megestrol Acetate USP | 4.000 |
| 2. Glycerol USP | 10.00 |
| 3. Sorbitol NF | 10.00 |
| 4. Polysorbate 80 | 0.030 |
| 5. Xanthan Gum NF | 0.220 |
| 6. Sodium Benzoate NF | 0.200 |
| 7. Citric Acid USP | 0.300 |
| 8. Sodium Citrate USP | 0.060 |
| 9. Sucrose NF | 5.000 |
| 10. Lemon Flavor | 0.080 |
| 11. Purified Water USP | 70.11 |

Preparation of the megestrol acetate suspension using the above-proportional amounts of ingredients is carried out as follows. Glycerol, sorbitol and polysorbate are combined in water to form a solution. Next, xanthan gum is added to this solution in order to uniformly hydrate the gum. The citrates, sucrose, sodium benzoate, and flavor are then added to the gum dispersion and the gum slurry passed through a screen. Next, megestrol acetate is added to the gum dispersion to provide a uniform suspension. The entire suspension is then passed through a colloid mill or homogenizer to provide an oral suspension containing 40 mg/ml of megestrol acetate.

EXAMPLE 3

A lemon-flavored oral suspension containing 60 mg of megestrol acetate per milliliter was prepared with a list of ingredients according to Table 4.

TABLE 4

Formulation for Megestrol Acetate Suspension

| Ingredients | % weight/volume |
| --- | --- |
| 1. Megestrol Acetate USP | 6.000 |
| 2. polyethylene glycol | 18.00 |
| 3. Docusate Sodium | 0.010 |
| 4. Xanthan Gum NF | 0.200 |
| 5. Sodium Benzoate NF | 0.200 |
| 6. Citric Acid USP | 0.300 |
| 7. Sodium Citrate USP | 0.060 |
| 8. Sucrose NF | 5.000 |
| 9. Lemon Flavor | 0.080 |
| 10. Purified Water USP | 70.15 |

Preparation of the megestrol acetate suspension using the above-proportional amounts of ingredients is carried out as follows. Polyethylene glycol and docusate sodium are combined in water to form a solution. Next, xanthan gum is added to this solution in order to uniformly hydrate the gum. The citrates, sucrose, sodium benzoate, and flavor are then added to the gum dispersion and the gum slurry passed through a screen. Next, megestrol acetate is added to the gum dispersion to provide a uniform suspension. The entire suspension is then passed through a colloid mill or homogenizer to provide an oral suspension containing 60 mg/ml of megestrol acetate.

EXAMPLE 4—Suspension Stability

The tendency of each suspension, prepared according to Examples 1–3, to flocculate was assessed as follows. Each suspension is allowed to settle in a controlled environment of 400° C., and 75% relative humidity for a period of 3 months. Following that, each of the sedimented suspensions was shaken and easily redispersed reforming the original suspension.

The invention has been described in terms of preferred embodiments thereof, but is more broadly applicable as will be understood by those skilled in the art. The scope of the invention is therefore limited only by the following claims.

What is claimed is:

1. An oral pharmaceutical composition in the form of a stable flocculated suspension in water capable of being redispersed after being allowed to settle at 40° C. and 75% relative humidity for a period of three months, said composition comprising:
   (a) about 10 to 200 mg per ml micronized megestrol acetate;
   (b) about 10 to 40% by weight of at least one compound selected from the group consisting of polyethylene glycol, propylene glycol, glycerol, and sorbitol; and
   (c) about 0.0001 to 0.03% by weight of a surfactant, wherein polysorbate and polyethylene glycol are not simultaneously present in said composition.

2. The composition of claim 1, wherein the surfactant comprises a hydrophobic moiety having a straight carbon chain of up to 20 atoms.

3. The composition of claim 2, wherein the straight carbon chain is less than 10 carbon atoms in length.

4. The composition of claim 1, wherein the surfactant is non-ionic.

5. The composition of claim 4, wherein the surfactant is selected from the group consisting of alkanolamides, ethoxylated alcohols, carboxylic acids, amines, alcohol amides, alcohol phenol, glyceryl esters, sorbitan esters, polyoxyethylene esters and phosphate esters.

6. The composition of claim 4, wherein the surfactant is polysorbate.

7. The composition of claim 4, wherein the surfactant is polyoxyethylene 2, 4, 6, 8, 12, 20, 30, 40, 50, 100, or 150 stearate.

8. The composition of claim 1, wherein the surfactant is cationic.

9. The composition of claim 8, wherein the surfactant is selected from the group consisting of cetyldimethylethylammonium bromide and quaternary amines.

10. The composition of claim 8, wherein the surfactant is cetyldimethylethylammonium bromide.

11. The composition of claim 1, wherein the surfactant is anionic.

12. The composition of claim 11, wherein the surfactant is selected from the group consisting of salts of sulphonic acids, fatty alkyl sulphosuccinates, fatty alkyl ether sulphosuccinates, acyl sarcosinates, acyl taurides, paraffin sulphonates and salts of alkaline earth metals.

13. The composition of claim 11, wherein the surfactant is docusate sodium.

14. The composition of claim 1, wherein the concentration of megestrol acetate is about 40 mg per ml.

15. The composition of claim 1, wherein component (b) comprises a mixture of two compounds.

16. The composition of claim 15, wherein the compounds are glycerol and sorbitol.

17. The composition of claim 16, wherein the concentration of each of glycerol and sorbitol is up to about 20% weight/volume.

18. An oral pharmaceutical composition in the form of a stable flocculated suspension in water comprising on a percent weight/volume basis about 4% megestrol acetate, about 0.0005–0.030% docusate sodium, up to about 20% glycerol, up to about 20% sorbitol, about 0.1–0.35% xanthan gum, about 0.1–0.3% sodium benzoate, about 0.3% citric acid, about 0.06% sodium citrate, about 5% sucrose, about 0.08% flavor, and the remainder water, wherein polysorbate and polyethylene glycol are not simultaneously present in said composition.

19. An oral pharmaceutical composition in the form of a stable flocculated suspension in water comprising on a percent weight/volume basis about 4% megestrol acetate, about 0.0005–0.030% polyoxyethylene 40 stearate, up to about 20% glycerol, up to about 20% sorbitol, about 0.1–0.35% xanthan gum, about 0.1–0.3% sodium benzoate, about 0.3% citric acid, about 0.06% sodium citrate, about 5% sucrose, about 0.08% flavor, and the remainder water, wherein polysorbate and polyethylene glycol are not simultaneously present in said composition.

* * * * *